United States Patent
Priore et al.

(10) Patent No.: US 9,041,932 B2
(45) Date of Patent: May 26, 2015

(54) CONFORMAL FILTER AND METHOD FOR USE THEREOF

(71) Applicant: CHEMIMAGE TECHNOLOGIES LLC, Pittsburgh, PA (US)

(72) Inventors: Ryan J. Priore, Wexford, PA (US); Thomas C. Voigt, Export, PA (US); Maxxwell A. R. Chatsko, Pittsburgh, PA (US); Patrick J. Treado, Pittsburgh, PA (US)

(73) Assignee: ChemImage Technologies LLC, Pittsburgh, PA (US)

( * ) Notice: Subject to any disclaimer, the term of this patent is extended or adjusted under 35 U.S.C. 154(b) by 167 days.

(21) Appl. No.: 13/734,024

(22) Filed: Jan. 4, 2013

(65) Prior Publication Data
US 2013/0176568 A1    Jul. 11, 2013

Related U.S. Application Data

(60) Provisional application No. 61/631,576, filed on Jan. 6, 2012.

(51) Int. Cl.
| | |
|---|---|
| *G01N 21/00* | (2006.01) |
| *G01J 3/51* | (2006.01) |
| *G01J 3/457* | (2006.01) |
| *G01N 21/35* | (2014.01) |

(Continued)

(52) U.S. Cl.
CPC .. *G01J 3/51* (2013.01); *G01J 3/457* (2013.01); *G01N 21/35* (2013.01); *G01J 2003/1213* (2013.01); *G01J 3/0224* (2013.01); *G01N 21/255* (2013.01); *G01N 21/33* (2013.01); *G01N 21/359* (2013.01); *G01N 21/65* (2013.01); *G01N 21/718* (2013.01); *G01N 2021/6471* (2013.01); *G01N 2201/067* (2013.01); *G01N 2201/129* (2013.01)

(58) Field of Classification Search
USPC .................. 356/301, 432–440, 416, 364–369
See application file for complete search history.

(56) References Cited

U.S. PATENT DOCUMENTS

| | | | |
|---|---|---|---|
| 6,234,250 B1 | 5/2001 | Green | |
| 6,588,505 B2 | 7/2003 | Beck | |

(Continued)

FOREIGN PATENT DOCUMENTS

| | | |
|---|---|---|
| AU | 2009354176 A1 | 1/2012 |
| AU | 2009354176 B2 | 9/2012 |

(Continued)

OTHER PUBLICATIONS

WO2006083720A3, International Search Report, Sep. 12, 2006.

(Continued)

*Primary Examiner* — Hoa Pham
(74) *Attorney, Agent, or Firm* — Pepper Hamilton LLP

(57) ABSTRACT

A system and method for detecting analytes using a conformal filter. A conformal filter, which may comprise a tunable filter, is configured to filter interacted photons conforming to a spectral shape correlated with an analyte of interest. Conformal filter configurations may be selected by consulting a modified look-up table associated with an analyte. An iterative methodology may be used to calibrate a conformal design for an analyte of interest, refine a previous conformal filter design for an analyte of interest, and/or generate a new conformal filter design for an analyte of interest.

34 Claims, 9 Drawing Sheets

(51) Int. Cl.
*G01J 3/02* (2006.01)
*G01N 21/25* (2006.01)
G01J 3/12 (2006.01)
G01N 21/33 (2006.01)
G01N 21/359 (2014.01)
G01N 21/65 (2006.01)
G01N 21/71 (2006.01)
G01N 21/64 (2006.01)

(56) References Cited

U.S. PATENT DOCUMENTS

| | | |
|---|---|---|
| 6,604,581 B2 | 8/2003 | Moake |
| 6,992,809 B1 | 1/2006 | Wang |
| 7,150,324 B2 | 12/2006 | Laursen |
| 7,336,323 B2 | 2/2008 | Wang |
| 7,362,489 B2 | 4/2008 | Wang |
| 7,411,796 B2 | 8/2008 | Lee |
| 7,428,045 B2 * | 9/2008 | Stewart et al. ............... 356/301 |
| 7,623,233 B2 | 11/2009 | Freese |
| 7,697,141 B2 | 4/2010 | Jones |
| 7,848,000 B2 | 12/2010 | Wang |
| 7,859,753 B2 | 12/2010 | Wang |
| 7,911,605 B2 | 3/2011 | Myrick |
| 7,920,258 B2 | 4/2011 | Myrick |
| 8,027,855 B2 | 9/2011 | Freese |
| 8,049,881 B2 | 11/2011 | Myrick |
| 8,154,726 B2 | 4/2012 | Blackburn |
| 8,184,295 B2 | 5/2012 | Myrick |
| 8,208,147 B2 | 6/2012 | Myrick |
| 8,212,213 B2 | 7/2012 | Myrick et al. |
| 8,213,006 B2 | 7/2012 | Myrick |
| 8,213,012 B2 | 7/2012 | Myrick |
| 8,237,920 B2 | 8/2012 | Jones |
| 8,237,929 B2 | 8/2012 | Myrick |
| 8,240,189 B2 | 8/2012 | Myrick |
| 8,283,633 B2 | 10/2012 | Myrick |
| 8,345,234 B2 | 1/2013 | Myrick |
| 8,352,205 B2 | 1/2013 | Myrick |
| 8,358,418 B2 | 1/2013 | Myrick |
| 8,379,199 B2 | 2/2013 | Freese et al. |
| 8,395,769 B2 * | 3/2013 | Stewart et al. ............... 356/301 |
| 8,400,637 B2 | 3/2013 | Myrick |
| 8,406,859 B2 | 3/2013 | Zuzak |
| 2001/0013410 A1 | 8/2001 | Beck |
| 2001/0013411 A1 | 8/2001 | Beck |
| 2001/0042617 A1 | 11/2001 | Beck |
| 2001/0043146 A1 | 11/2001 | Beck |
| 2003/0192689 A1 | 10/2003 | Moake |
| 2004/0065475 A1 | 4/2004 | Laursen |
| 2007/0294094 A1 | 12/2007 | Alessandrini |
| 2009/0002697 A1 | 1/2009 | Freese |
| 2010/0198080 A1 | 8/2010 | Liu |
| 2010/0245096 A1 | 9/2010 | Jones |
| 2010/0265509 A1 | 10/2010 | Jones |
| 2011/0021908 A1 | 1/2011 | Lee |
| 2011/0104071 A1 | 5/2011 | Lee |
| 2011/0218736 A1 | 9/2011 | Pelletier |
| 2011/0271738 A1 * | 11/2011 | McGill et al. ............... 73/23.41 |
| 2011/0279744 A1 | 11/2011 | Voigt |
| 2012/0018152 A1 | 1/2012 | Zuilekom |
| 2012/0062888 A1 | 3/2012 | Voigt |
| 2012/0150164 A1 | 6/2012 | Lee |
| 2012/0150451 A1 | 6/2012 | Skinner |
| 2012/0211650 A1 | 8/2012 | Jones |
| 2012/0268730 A1 | 10/2012 | Myrick |
| 2012/0279281 A1 | 11/2012 | Myrick |
| 2012/0300143 A1 | 11/2012 | Voigt |
| 2013/0201469 A1 * | 8/2013 | Treado et al. ............... 356/39 |
| 2013/0321813 A1 * | 12/2013 | Treado et al. ............... 356/416 |
| 2014/0198315 A1 * | 7/2014 | Priore et al. ............... 356/364 |

FOREIGN PATENT DOCUMENTS

| | | |
|---|---|---|
| CA | 2596251 A1 | 8/2006 |
| CA | 2654783 A1 | 3/2011 |
| CA | 2765477 A1 | 4/2011 |
| GB | 2390423 A | 1/2004 |
| WO | WO0118357 A2 | 3/2001 |
| WO | WO0235059 A1 | 5/2002 |
| WO | WO2004033841 A2 | 4/2004 |
| WO | WO2006083720 A2 | 8/2006 |
| WO | WO2006116031 A1 | 11/2006 |
| WO | WO2007062201 A1 | 5/2007 |
| WO | WO2007062202 A1 | 5/2007 |
| WO | WO2007062224 A1 | 5/2007 |
| WO | WO2007064575 A1 | 6/2007 |
| WO | WO2007064578 A2 | 6/2007 |
| WO | WO2007064579 A1 | 6/2007 |
| WO | WO2008057905 A2 | 5/2008 |
| WO | WO2008121715 A1 | 10/2008 |
| WO | WO2012108885 A1 | 8/2010 |
| WO | WO2012108886 A1 | 8/2010 |
| WO | WO2010120285 A1 | 10/2010 |
| WO | WO2011049571 A1 | 4/2011 |
| WO | WO2011063086 A1 | 5/2011 |
| WO | WO2012161694 A1 | 11/2012 |
| WO | WO2012166138 A1 | 12/2012 |

OTHER PUBLICATIONS

WO2008057905A3, International Search Report, May 9, 2008.
WO2007064578A3, International Search Report, Mar. 25, 2008.
WO2001018357A3, International Search Report, Mar. 1, 2001.

* cited by examiner

CONFORMAL FILTER AND METHOD FOR USE THEREOF

RELATED APPLICATIONS

This application claims benefit under 35 USC §119(e) to U.S. Provisional Patent Application No. 61/631,576, entitled "Conformal Filter and Method for Use Thereof," filed on Jan. 6, 2012, which is hereby incorporated by reference its entirety.

BACKGROUND

Spectroscopic imaging combines digital imaging and optical spectroscopy techniques, which can include Raman scattering, fluorescence, photoluminescence, laser induced breakdown, ultraviolet, visible and infrared absorption spectroscopies. When applied to the chemical analysis of materials, spectroscopic imaging is also referred to as chemical imaging. Instruments for performing spectroscopic (i.e. chemical) imaging typically comprise an illumination source, image gathering optics, focal plane array imaging detectors and imaging spectrometers.

In general, the size or accessibility of a sample determines the choice of image gathering optic. For example, a microscope is typically employed for the analysis of sub-micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, or for objects located at a significant stand-off distance from a sensor, telescopes are appropriate image gathering optics.

Two-dimensional, imaging focal plane array (FPA) detectors are typically employed to detect images formed by the various optical systems. The choice of FPA detector is governed by the spectroscopic technique employed to characterize the sample of interest. For example, silicon (Si) charge-coupled device (CCD) detectors or complementary metal-oxide-semiconductor (CMOS) detectors are typically employed with visible wavelength fluorescence and Raman spectroscopic imaging systems, while indium gallium arsenide (InGaAs) FPA detectors are typically employed with near infrared spectroscopic imaging systems.

Conventional spectroscopic devices operate over a limited range of wavelengths due to the operation ranges of the detectors or imaging spectrometers possible. This enables analysis in the ultraviolet (UV), visible (VIS), near infrared (NIR), short wave infrared (SWIR), mid infrared (MIR), and long wave infrared (LWIR) wavelengths, as well as some overlapping ranges. These correspond to wavelengths of about 180-380 nm (UV), about 380-700 nm (VIS), about 700-2500 nm (NIR), about 850-1700 nm (SWIR), about 700-1700 (VIS-NIR), about 2500-5000 nm (MIR), and about 5000-25000 (LWIR).

Spectroscopic imaging of a sample is commonly implemented by one of two methods. First, point-source illumination can be used on a sample to measure the spectra at each point of the illuminated area. Second, spectra can be collected over the entire area encompassing a sample simultaneously using an electronically tunable optical imaging filter such as an acousto-optic tunable filter (AOTF), a multi-conjugate tunable filter (MCF), or a liquid crystal tunable filter (LCTF). Here, the organic material in such optical filters is actively aligned by applied voltages to produce the desired bandpass and transmission function. The spectra obtained for each pixel of an image forms a complex data set referred to as a hyperspectral image. Hyperspectral images may contain the intensity values at numerous wavelengths or the wavelength dependence of each pixel element in the image. Multivariate routines, such as chemometric techniques, may be used to convert spectra to classifications.

Currently, tunable optical filter technology is limited to single bandpass, low throughput operation. Therefore, multiple, discrete bandpass measurements are required for analyte discrimination. The need for multiple measurements translates directly into overall measurement time.

Multivariate Optical Computing (MOC) is an approach which utilizes a compressive sensing device (e.g. an optical computer) to analyze spectroscopic data as it is collected. Other approaches utilize hard coated optical computing filters such as Multivariate Optical Elements (MOEs). MOEs are application-specific optical thin film filters that are used in transmission and reflectance modes. The radiometric response of a MOE-based instrument is proportional to the intended analyte in an associated matrix. While compressive sensing holds potential for decreasing measurement time, the use of MOEs have limitations. For example, MOEs are fixed and lack flexibility for adapting to different analytes.

There exists a need for an adaptable filter that can be used to detect a wide variety of analytes while reducing overall measurement time.

SUMMARY

The present disclosure provides for an adaptable tunable filter with the flexibility of conforming to a specific, broadband spectral feature (e.g. pattern or shape). This filter, referred to herein as a "conformal filter," overcomes the limitations of the prior art by simultaneously transmitting multiple passbands that improve discrimination performance for analytes (e.g., discriminating between a target analyte and background), by increasing the throughput of a tunable filter and by increasing the speed of analysis.

The present disclosure provides for a system and method for detecting analytes using a conformal filter. A system of the present disclosure provides for a conformal filter comprising a tunable filter capable of adapting to a variety of configurations which filter interacted photons conforming to at least one spectral shape associated with an analyte of interest. Each configuration is designed to filter interacted photons conforming to at least one spectral shape associated with an analyte of interest. The conformal filter may be configured to operate in conjunction with a look-up table (LUT), providing flexibility for detecting multiple analytes of interest in near real-time. The LUT may comprise at least one voltage associated with each stage of the tunable filter. Each voltage is configured to cause the tunable filter to conform to a spectral shape associated with the analyte when applied to the associated stage.

A conformal filter as provided for herein is adaptable and may be configured to detect a wide variety of analytes. The conformal filter may also be used to detect analytes using a variety of spectroscopic and chemical imaging modalities.

The present disclosure provides for a method for detecting one or more analytes of interest using a conformal filter. A sample is illuminated to generate at least one plurality of interacted photons which are passed through a conformal filter. A test data set is generated which is representative of the sample. This test data set may then be analyzed to assess the sample for one or more characteristics of the analyte.

The present disclosure also provides for a system comprising a processor and a non-transitory processor-readable storage medium in operable communication with the processor. The storage medium may contain one or more programming instructions that, when executed, cause the processor to tune a conformal filter to a configuration to filter interacted photons conforming to a spectral shape associated with an analyte of interest, generate a test data set representative of the sample, and analyze the test data set to assess the sample for at least one characteristic of the analyte.

BRIEF DESCRIPTION OF THE DRAWINGS

The accompanying drawings, which are included to provide further understanding of the disclosure and are incorporated in and constitute a part of this specification illustrate embodiments of the disclosure, and together with the description, serve to explain the principles of the disclosure.

FIG. 1A is illustrative of a conformal filter embodiment. FIG. 1B is illustrative of a conformal filter embodiment comprising a rotatable aperture. FIG. 1C is illustrative of a conformal filter embodiment comprising a MCF design.

FIG. 5A illustrates an exemplary experimental set up comprising ammonium nitrate (AN), ammonium sulfate (AS), and urea samples. FIG. 5B illustrates imaging results using a method of the present disclosure. FIG. 5C illustrates detection performance for discriminating between AN and AS.

DETAILED DESCRIPTION

Figure 1A:
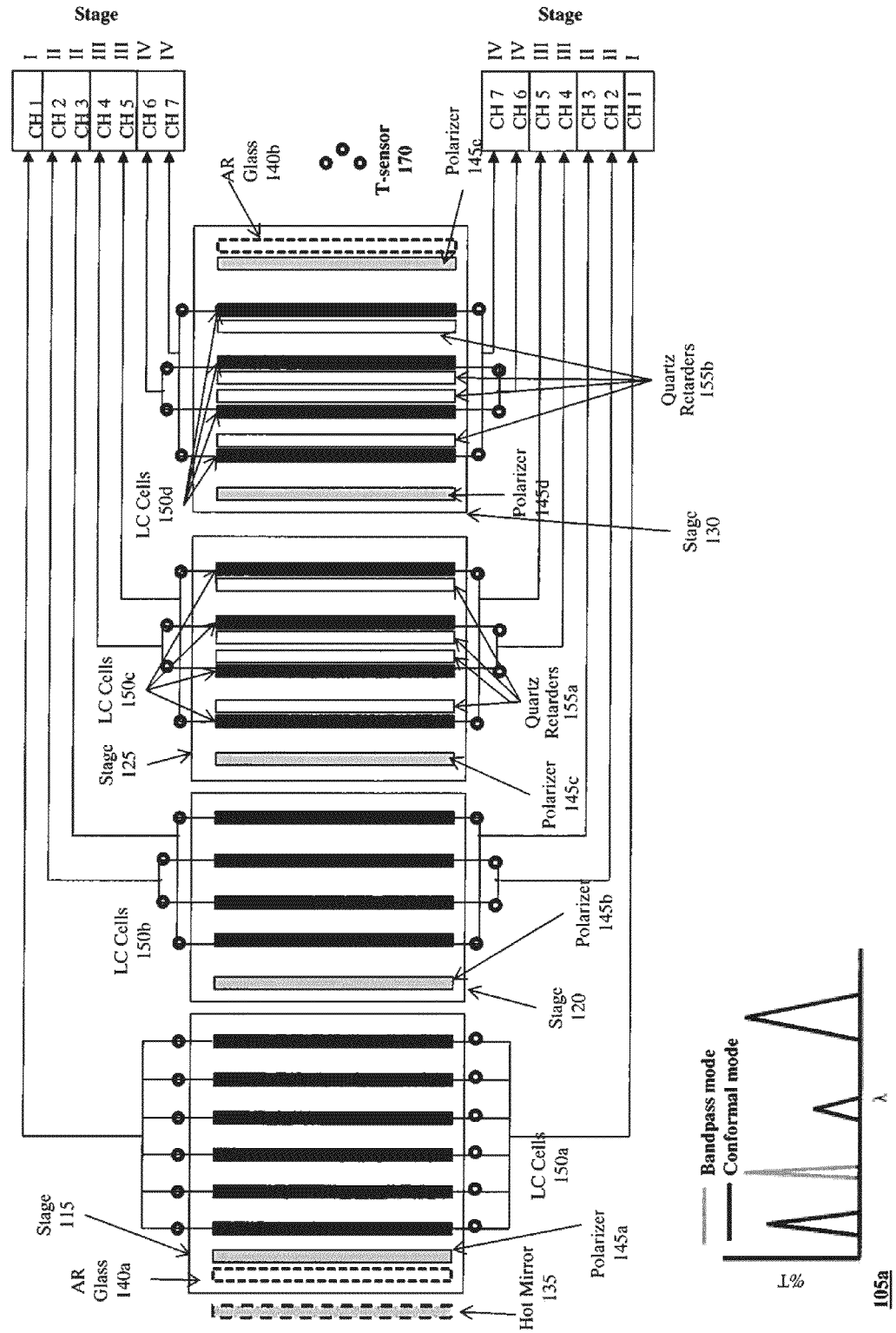
FIGS. 1A-1C are illustrative of exemplary conformal filter embodiments of the present disclosure.

Reference will now be made in detail to the embodiments of the present disclosure, examples of which are illustrated in the accompanying drawings. Wherever possible, the same reference numbers will be used throughout the specification to refer to the same or like parts.

The present disclosure provides for a system and method for detecting analytes of interest using a conformal filter. In one embodiment, the present disclosure provides for a system comprising a conformal filter and an associated LUT. The conformal filter may comprise a tunable filter, which is traditionally intended for single bandpass transmission, which is designed to enable tuning to a plurality of different configurations. Each configuration may be designed to filter interacted photons, generated by illuminating a sample, that conform to one or more spectral shapes associated with an analyte of interest. Interacted photons may comprise at least one of the following: photons absorbed by a sample, photons reflected by a sample, photons scattered by a sample, and photons emitted by a sample.

Conformal filter configurations may be determined by consulting the LUT, which corresponds to the analyte. The LUT may comprise at least one voltage associated with each stage of the tunable filter. These voltages may be such that when applied to the associated stage, the tunable filter conforms to a spectral shape associated with the analyte. LUTs may be modified, providing the appropriate conformal filter configurations for detecting a variety of different analytes.

Examples of tunable filters that may be configured for use as a conformal filter may include: a liquid crystal tunable filter, an acousto optical tunable filter, a Lyot liquid crystal tunable filter, an Evans Split-Element liquid crystal tunable filter, a Solc liquid crystal tunable filter, a Ferroelectric liquid crystal tunable filter, Fabry Perot liquid crystal tunable filter, and combinations thereof. In one embodiment, the tunable filter may comprise a MCF. A MCF is an imaging filter with serial stages along an optical signal path in a Solc filter configuration. Angularly distributed retarder elements of equal birefringence are stacked in each stage, with a polarizer between stages. The retarders can include tunable (such as abutted liquid crystals tuned in unison), fixed and/or combined tunable and fixed birefringences. In one embodiment, quartz retarders may be used. Although the retardations are equal within each stage, distinctly different retardations may be used for two or more different stages. This causes some stages to pass narrow bandpass peaks and other stages to have widely spaced bandpass peaks. The transmission functions of the serial stages are superimposed with selected tunable peaks coinciding. The resulting conjugate filter has a high finesse ratio and good out of band rejection.

In one embodiment, the MCF may comprise filter technology available from ChemImage Corporation, Pittsburgh, Pa. This technology is further described in the following U.S. patents and published U.S. Patent Applications, which are hereby incorporated by reference in their entireties: U.S. Pat. No. 6,992,809, entitled "Multi-Conjugate Liquid Crystal Tunable Filter," U.S. Pat. No. 7,362,489, also entitled "Multi-Conjugate Liquid Crystal Tunable Filter," No. 2012/0300143, entitled "VIS-SNIR Multi-Conjugate Liquid Crystal Tunable Filter," and No. 2011/0279744, entitled "Short Wave Infrared Multi-Conjugate Liquid Crystal Tunable Filter."

Figure 1B:
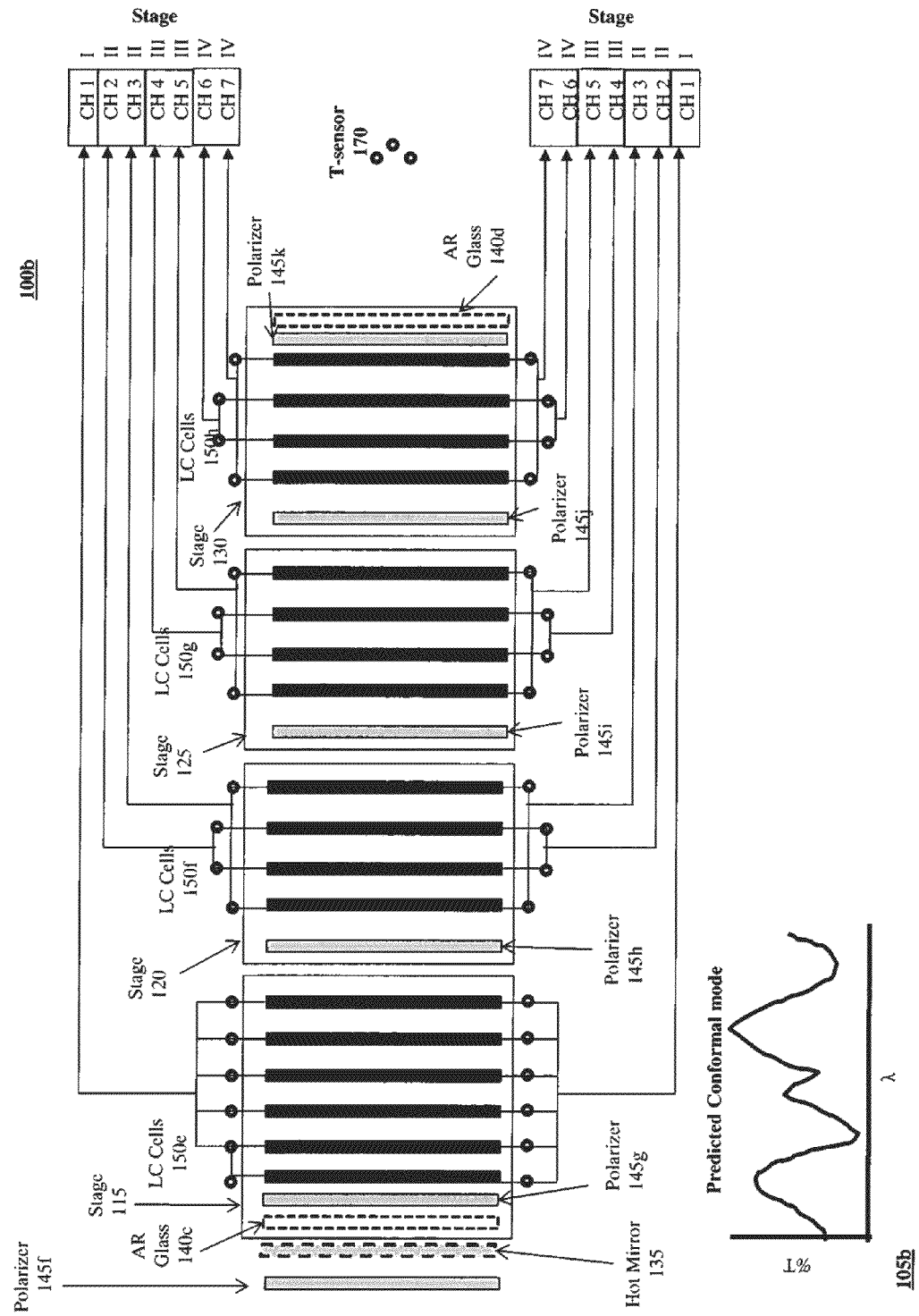
Figure 1C:
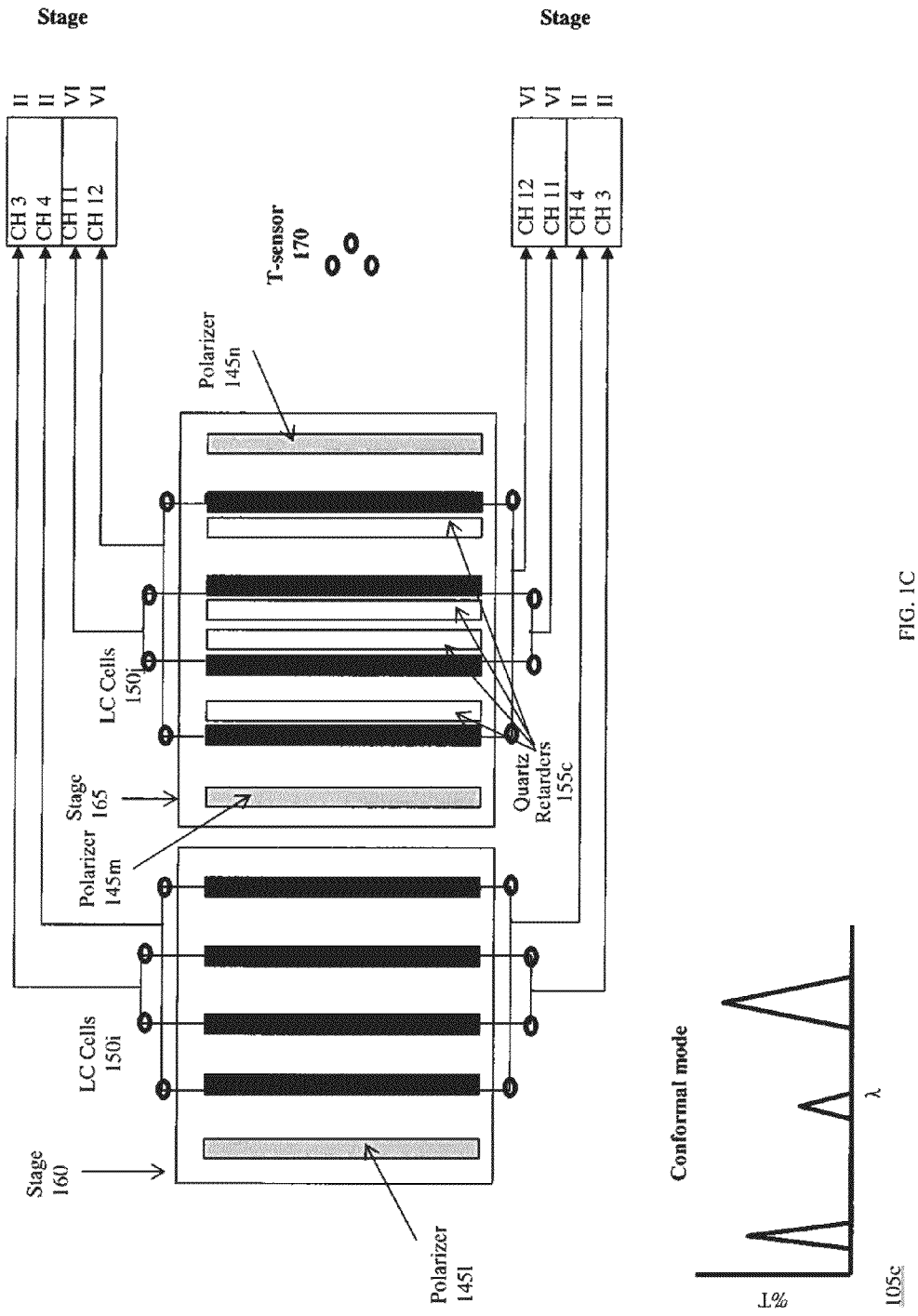

FIGS. 1A-1C illustrate conformal filter embodiments comprising a MCF which may operate in conjunction with one or more LUTs (not illustrated). In FIG. 1A, a hot mirror 135 may be operatively coupled to the MCF. A plurality of filter stages, 115, 120, 125, and 130 may be arranged in a Solc configuration. Each stage may comprise a combination of polarizers 145a-145d, liquid crystal (LC) cells 150a-150d, and quartz retarders 155a-155b. A first antireflective (AR) glass component 140a may be placed in front of the first polarizer 145a and a second AR glass component 140b may be placed after the last polarizer 145e. The filter may be operatively coupled to a temperature sensor 170 for monitoring the temperature of the filter and modifying the LUT as needed for temperature adjustments. Predicted transmission of the filter operating in both a bandpass and a conformal mode is also provided 110.

In FIG. 1B, the MCF 100b may comprise a polarizer 145f operatively coupled to the hot mirror 135 at an input of the MCF. The polarizer may be mounted to a rotatable aperture for increasing optical throughput. In one embodiment, the polarizer 145f may be at least one of the following: a mechanically rotatable polarizer and an electronically tunable LC cell. The polarizer 145f may be tuned as needed each time the MCF is tuned to a new configuration. Filter stages 115, 120, 125, and 130 may further comprise a combination of polarizers 145h-145k and liquid crystal (LC) cells 150e-150h. A first antireflective (AR) glass component 140c may be placed in front of polarizer 145g and a second AR glass component 140d may be placed after the last polarizer 145k. Predicted transmission of the MCF operating in conformal mode is also provided 105b.

In another embodiment, the present disclosure provides for a conformal filter comprising a modified MCF. In such an embodiment, a tunable filter may be modified or specifically designed so that selected individual stages of a traditional tunable filter comprise multiple, lower resolution liquid crystal cells. As illustrated by FIG. 1C, a MCF may be redesigned with fewer stages 160 and 165 for use as a conformal filter 100c. Selected filter stages 160 and 165 may comprise a combination of optical elements including polarizers 145*l*-145*n*, LC cells 150*l*-150*j*, and quartz retarders 155c. Predicted transmission of the conformal filter is also provided 105c. The present disclosure contemplates that other configurations may be used to modify the MCF and that the present disclosure is not intended to be limited to the design in FIG. 1C. Other conformal filter designs may be selected using a robust, iterative, non-linear optimization methodology. Such a methodology may begin with a random starting configuration and be reconfigured until a minimum response is achieved. The present disclosure contemplates that any iterative, non-linear optimization method known in the art may be applied to design the conformal filter.

Figure 2:
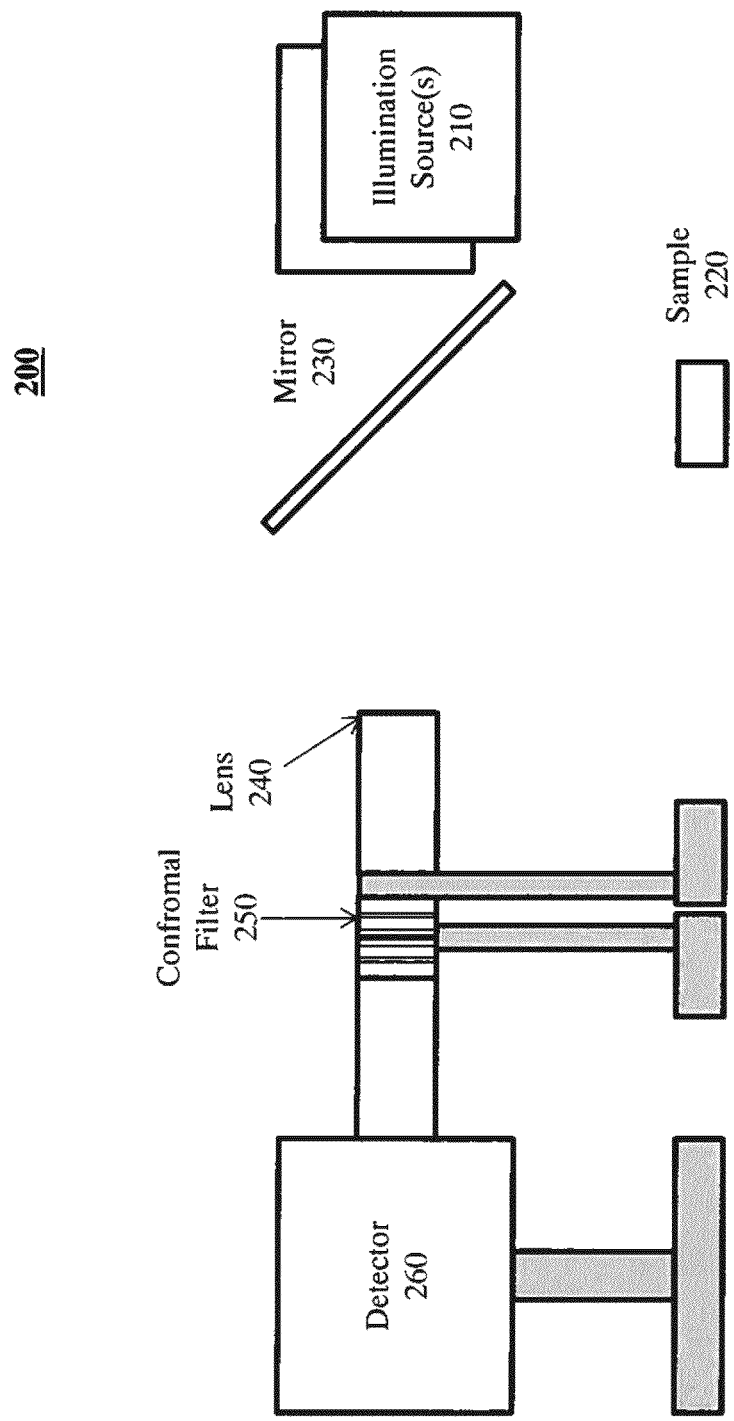
FIG. 2 is illustrative of a system of the present disclosure.

The present disclosure also provides for a system comprising a conformal filter, one embodiment of which is illustrated in FIG. 2. The system 200 may comprise at least one illumination source 210 for illuminating a sample 220 to generate at least one plurality of interacted photons. The present disclosure contemplates embodiments which may utilize active or passive illumination sources. In one embodiment, a broadband light source may be used. Examples of broadband illumination sources may include, but are not limited to: a quartz tungsten halogen lamp, a high-pressure mercury arc lamp, solar radiation, a light emitting diode, a blackbody emitter, and combinations thereof. In an embodiment comprising active illumination, a laser illumination source may be used. These interacted photons may be directed via a mirror or other component 230 through a lens 240, a conformal filter 250, and to a detector 260. In one embodiment, the detector 260 may comprise an InGaAs detector, a CCD detector, a CMOS detector, an InSb detector, a MCT detector, and combinations thereof. In one embodiment, the system 200 may further comprise a LUT corresponding to one or more analytes. The system 200 may further comprise one or more processors for operating system components, storing LUTs, and/or storing test data and/or reference data.

Figure 3:
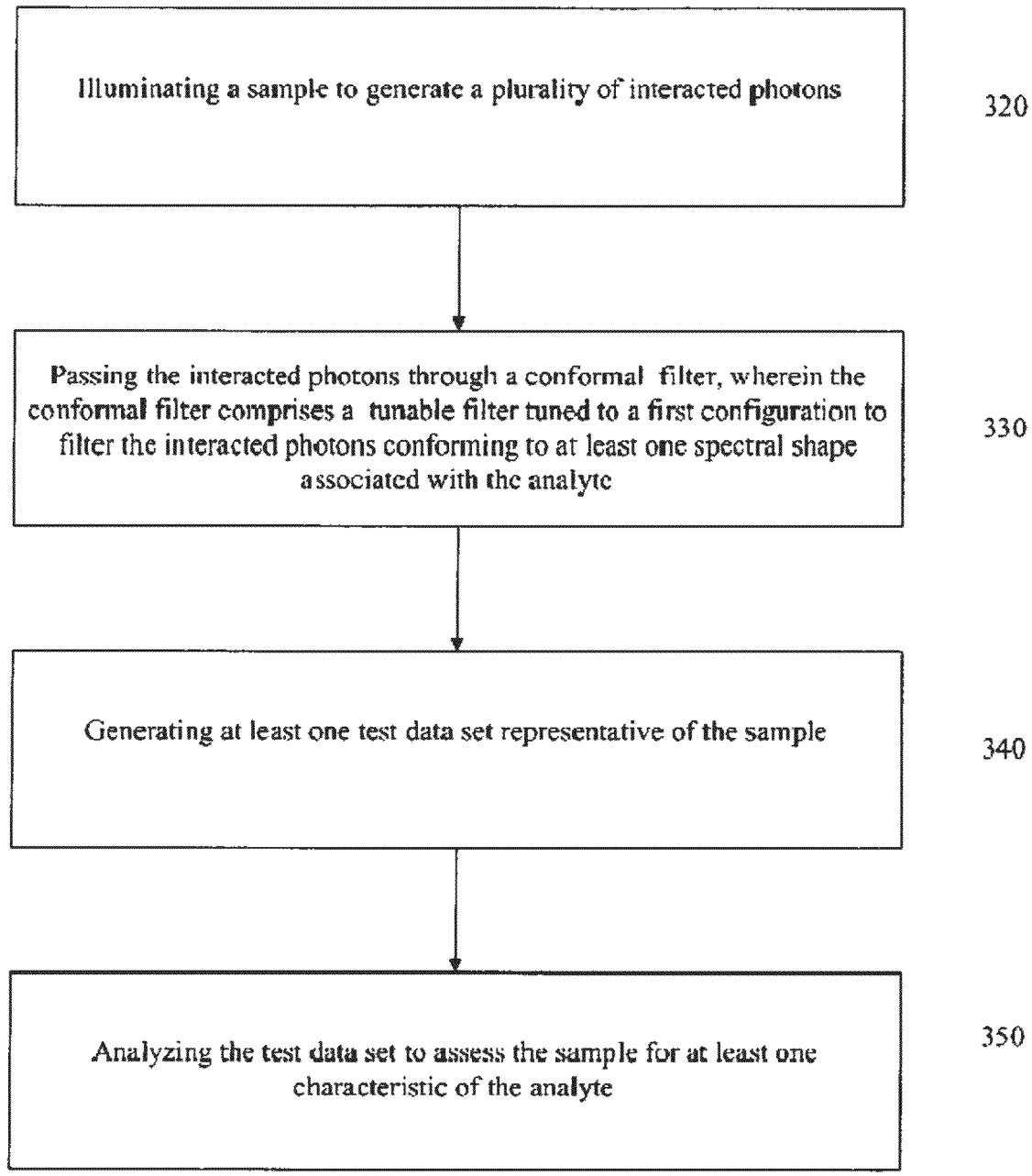
FIG. 3 is representative of a method of the present disclosure.

The present disclosure also provides for a method of assessing samples for characteristics of an analyte of interest. One embodiment illustrated by FIG. 3. A sample may be illuminated in step 320 to generate a plurality of interacted photons. In one embodiment, the sample may be illuminated using wide-field illumination.

In step 330, the interacted photons may be passed through a conformal filter. In one embodiment, the conformal filter comprises a tunable filter tuned to a first configuration to filter the interacted photons conforming to at least one spectral shape associated with the analyte. Tunable filter configurations may be determined by searching a LUT associated with the analyte.

At least one test data set representative of the sample may be generated in step 340. In one embodiment, the at least one test data set may comprise at least one of the following: a Raman test data set, an IR test data set, a VIS test data set, a UV test data set, a VIS-NIR test data set, a LIBS test data set, and a fluorescence test data set. The at least one test data set may comprise at least one of the following: a SWIR test data set, a MWIR test data set, and a LWIR test data set.

In one embodiment, the at least one test data set may comprise at least one intensity measurement as a function of wavelength. In such an embodiment, utilizing a conformal filter provides for generating a spectral intensity that exploits full spectrum information without the need of generating a full spectrum. In another embodiment, the at least one test data set may comprise at least one spectral image. This spectral image may comprise an image wherein each pixel of the image is the intensity measurement of the analyte of interest at that location. In such an embodiment, utilizing a conformal filter of the present disclosure provides for the generation of a spectral image that exploits hyperspectral information without the need of generating the full hypercube.

The test data set may be analyzed in step 350 to assess at least one characteristic of the sample. The present disclosure contemplates that quantitative and/or qualitative characteristics of a sample may be assessed. Examples of sample characteristics that may be analyzed include, but are not limited to: the presence of the analyte in the sample, the absence of the analyte in the sample, a classification (e.g. class membership) of the analyte, a non-classification of the analyte, a concentration of the analyte, and combinations thereof.

The present disclosure also provides for a method for selecting a conformal filter configuration using an iterative process. This method is referred to herein as Real-time Contrast Enhancement (RtCE) and provides for configurations with high analyte specificity and sensitivity by applying active tunable filter voltage adjustment and feedback from a live measurement scene. Such an approach may be used to calibrate a conformal design for an analyte of interest, refine a previous conformal filter design for an analyte of interest, and/or generate a new conformal filter design for an analyte of interest.

Figure 4:
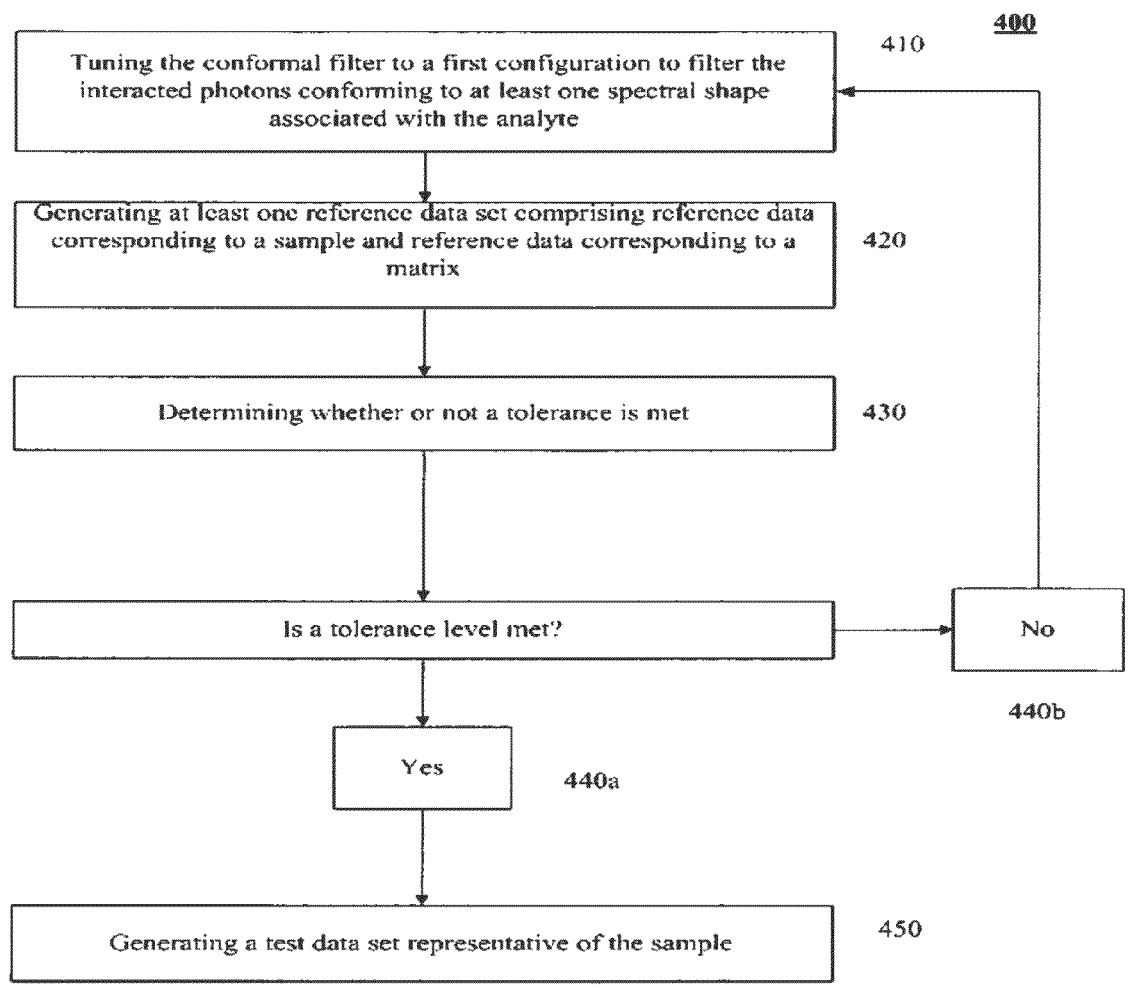
FIG. 4 is representative of a method of the present disclosure.

One embodiment of this optimization process is provided in FIG. 4. The method 400 may comprise tuning a conformal filter to a first configuration to filter interacted photons conforming to at least one spectral shape associated with an analyte in step 410. In step 420, at least one reference data set may be generated comprising reference data corresponding to a sample and reference data corresponding to a matrix. In one embodiment, the reference data set may comprise at least one reference spectrum associated with the sample and at least one reference spectrum associated with the matrix.

In another embodiment, the at least one reference data set may comprise at least one reference image comprising the sample and the matrix. A first region of interest may be selected corresponding to the sample and a second region of interest may be selected corresponding to the matrix. Spectral data may be extracted from these regions of interest.

In one embodiment, at least one chemometric technique may be applied to the at least one reference data set (e.g. spectral data). Examples of chemometric techniques include, but are not limited to: correlation analysis, principle component analysis, principle component regression, partial least squares, multivariate curve resolution, Mahalanobis distance, Euclidian distance, band target entropy, band target energy minimization, partial least squares discriminant analysis, adaptive subspace detection, and combinations thereof. Chemometric techniques may be used to compare test data to reference data.

One or more optical computations may also be applied to the test data set. In one embodiment, this optical computation may comprise at least one of the following: $T_1$, $T_1-T_2$, and $(T_1-T_2)/(T_1+T_2)$. Other optical computations known in the art may also be applied and the present disclosure should not be construed as to be limited to those specified herein.

A determination of whether or not a tolerance level is met may be made in step 430. In one embodiment, this determination may comprise applying at least one Figure of Merit (FOM) A FOM is a numerical value that may be used to guide the optimization process. Examples of figures of merit that may be applied include, but are not limited to: Standard error of calibration (SEC), Euclidian Distance, standard error of prediction (SEP), 1-Area Under the Receiver Operator Characteristic Curve (AUROC), optical throughput (% T), and combinations thereof. Other FOMs may be used that incorporate optical throughput, signal to noise ratio (SNR), among others. If a tolerance level is met 440a, then a test data set representative of the sample may be generated in step 450. If a tolerance level is not met 440b, then the process may be repeated for at least one other conformal filter configuration until a tolerance level is met.

In another embodiment, the present disclosure provides for a system comprising a processor and a non-transitory processor-readable storage medium in operable communication with the processor. The storage medium may contain one or more programming instructions that, when executed, cause the processor to tune the a conformal filter to a first configuration and filter interacted photons conforming to at least one spectral shape associated with an analyte of interest, generate at least one test data set representative of the sample, and analyze the test data set to assess the sample for at least one characteristic of the analyte. The storage medium may further contain programming instructions that cause the processor to select conformal filter configurations by searching a LUT corresponding to an analyte and applying the configuration to the conformal filter.

In another embodiment, the system may further comprise one or more programming instructions that, when executed, cause the processor to iteratively configure the conformal filter until a tolerance level is met. In such an embodiment, the instructions may cause the processor to tune the conformal filter to a first configuration to filter interacted photons conforming to at least one spectral shape associated with the analyte, generate at least one reference data set comprising reference data corresponding to the sample and reference data corresponding to a matrix, and determine whether or not a tolerance level is met. If a tolerance level is met, a test data set ay be generated. If a tolerance level is not met, then the steps may be repeated for one or more difference configurations until a tolerance level is met. In one embodiment, whether or not a tolerance level is met may be determined by the processor applying at least one figure of merit. In other embodiments the processor may further analyze the test data set by applying at least one of the following: an optical computation and a chemometric technique.

EXAMPLES

Figure 5A:
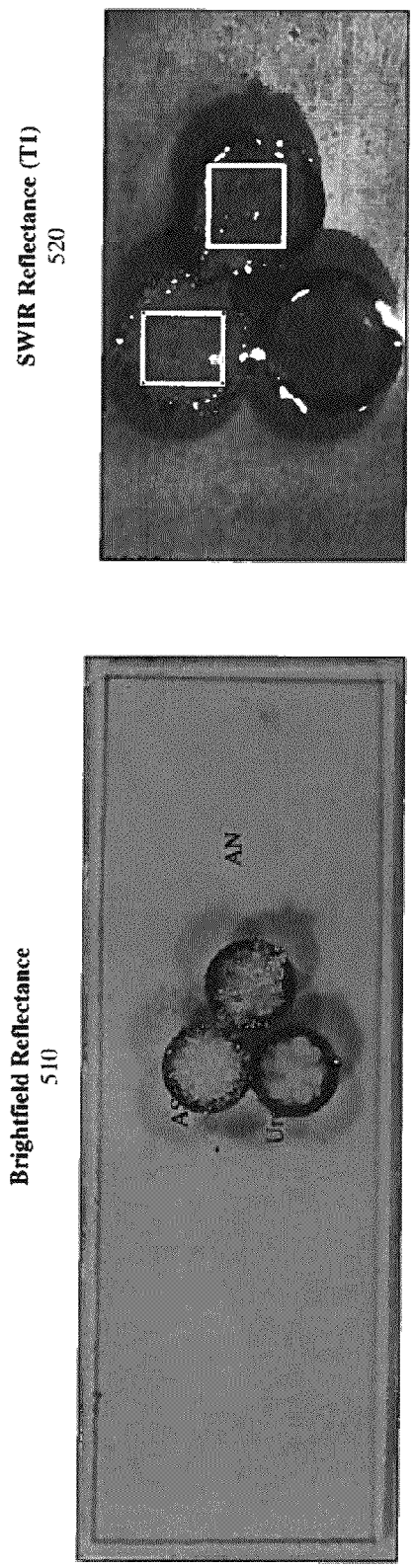
FIGS. 5A-5C are illustrative of the detection capabilities of a conformal filter of the present disclosure.
Figure 5A:
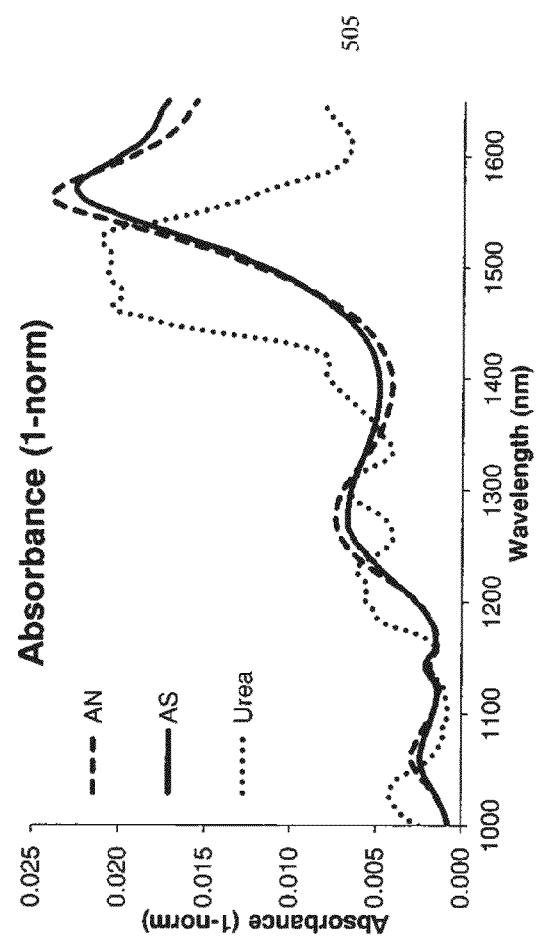
Figure 5B:
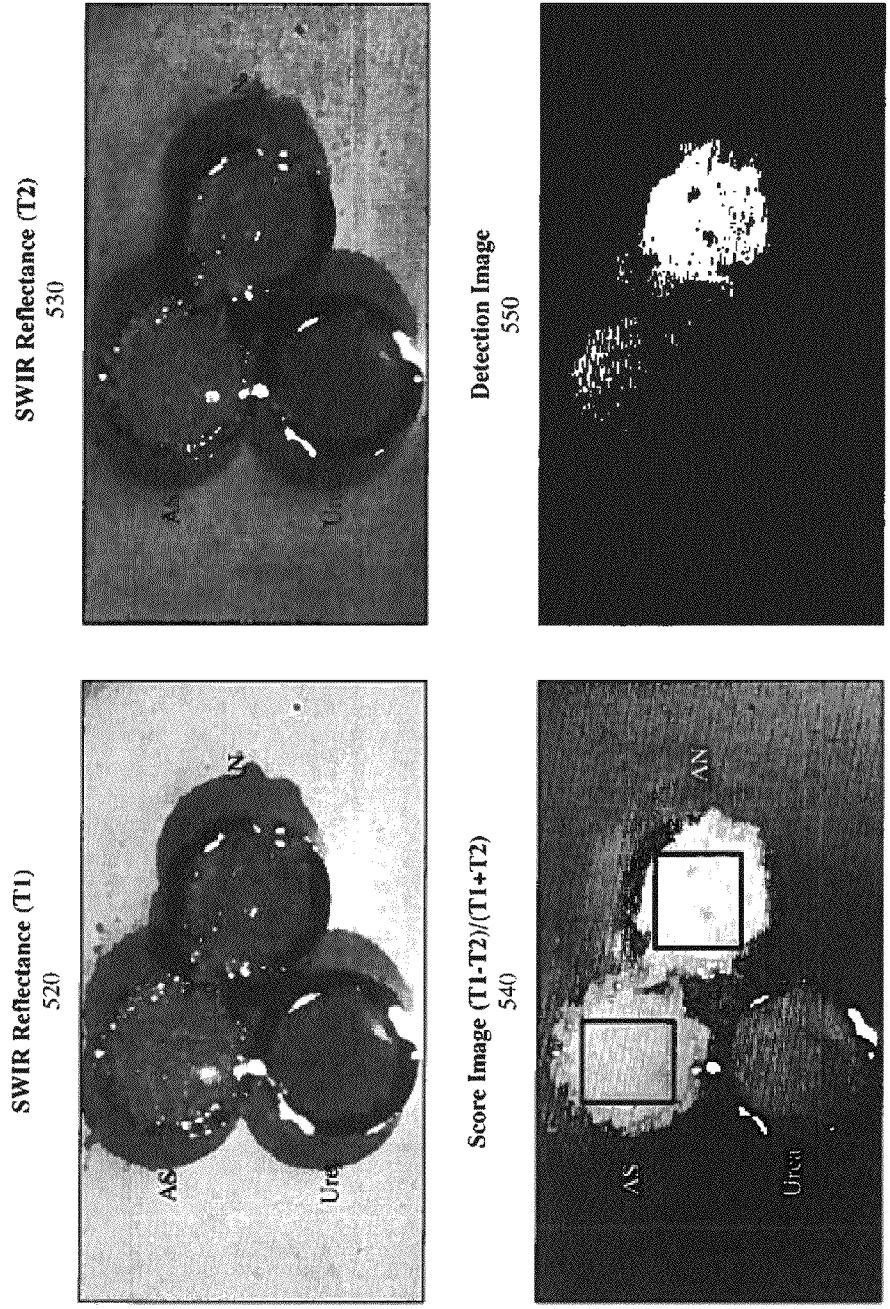
Figure 5C:
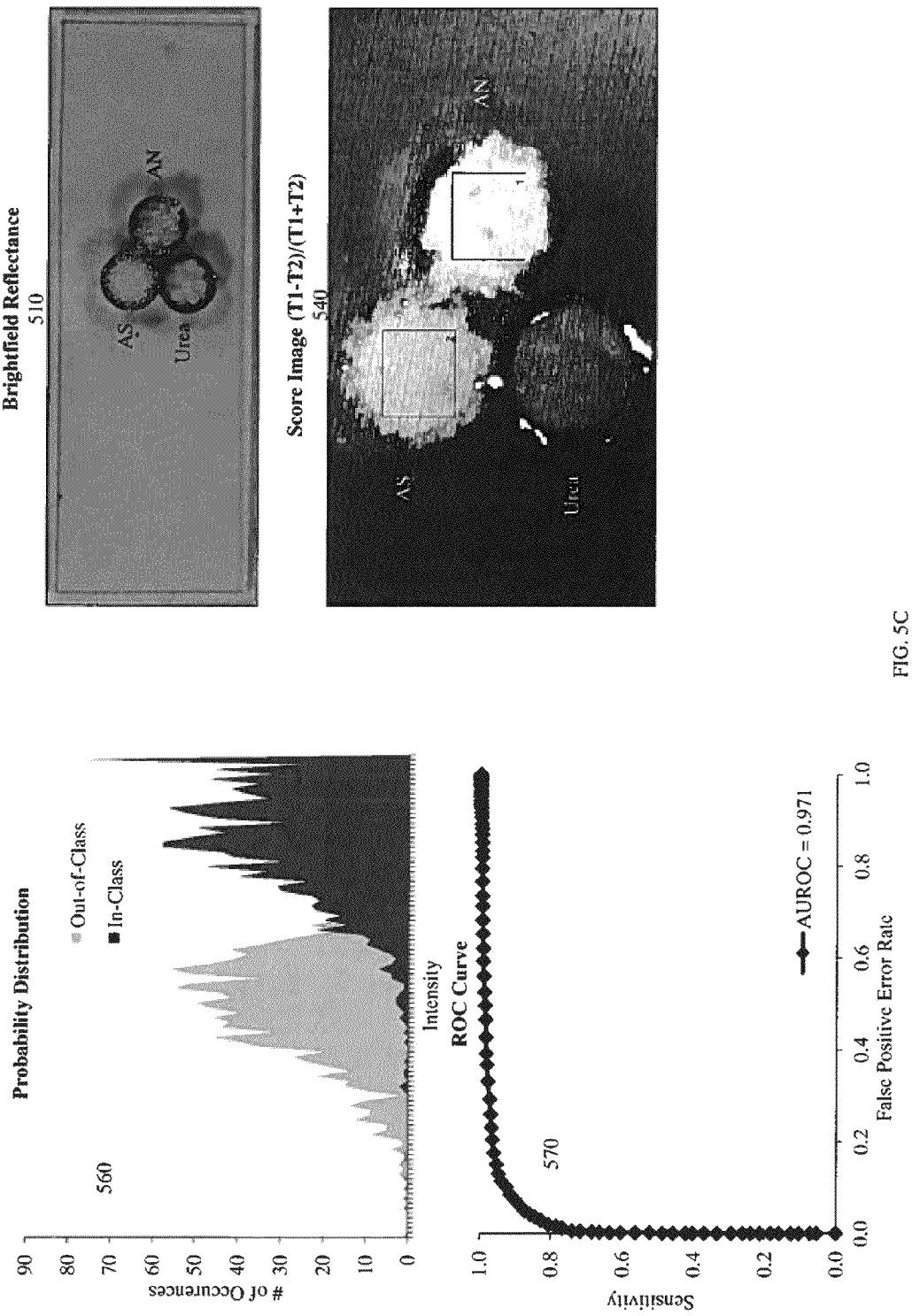

FIGS. 5A-5C are illustrative of the detection capabilities of a conformal filter of the present disclosure. Three samples were prepared comprising AS, AN, and urea. AN was selected as the analyte of interest, AS was selected as a confusant (background), and urea was selected as an interferent. The samples were analyzed using an experimental set up as represented by FIG. 2 wherein the illumination source 210 comprised a quartz tungsten halogen lamp, the conformal filter 250 comprised a MCF, and the detector 260 comprised a SWIR camera. A brightfield reflectance image 510 and a SWIR reflectance image ($T_1$) 530 were generated. Spectral data for each substance 505 is also illustrated in FIG. 5A, FIG. 5B illustrates the detection capabilities of the present disclosure when an RtCE methodology is applied. A second SWIR reflectance image ($T_2$) was generated 530. The optical computation ($T_1-T_2$)/($T_1+T_2$) was applied, and a score image 540 was generated. As can be seen from the detection image 550, AN was easily detected and distinguished from AS and urea. FIG. 5C is illustrative of the detection results after applying additional processing steps such as contrast flip and saturation removal. A probability distribution 560, from the score image 540, illustrates in-class v. out-of-class detections. The ROC curve 570 illustrates the sensitivity and false positive results achieved and was generated by applying a threshold to the probability distribution 560. As illustrated by the Examples, the system and method of the present disclosure hold potential for detecting analytes and discriminating between "near neighbors," i.e., analytes with similar spectral features.

While the disclosure has been described in detail in reference to specific embodiments thereof, it will be apparent to one skilled in the art that various changes and modifications can be made therein without departing from the spirit and scope of the embodiments. Additionally, while the examples provided herein related to specific analytes, the present disclosure is not limited to these analytes and may be used to detect a wide variety of analytes of interest. Thus, it is intended that the present disclosure cover the modifications and variations of this disclosure provided they come within the scope of the appended claims and their equivalents.

What is claimed is:

1. A method comprising:
    illuminating a sample to generate a plurality of interacted photons;
    passing the interacted photons through a conformal filter comprising a tunable filter having a plurality of filter stages;
    tuning the conformal filter to filter a first configuration of the plurality of interacted photons by:
        searching a look-up table comprising at least one voltage associated with each stage of the plurality of filter stages
        applying the at least one voltage to each stage of the plurality of filter stages to conform the tunable filter to at least one spectral shape associated with an analyte and
        generating a first plurality of filtered photons representative of the at least one spectral shape;
    generating at least one first test data set representative of the first plurality of filtered photons; and
    analyzing the at least one first test data set to identify at least one characteristic of the analyte.

2. The method of claim 1, wherein the at least one characteristic comprises one or more of a presence of the analyte in the sample, an absence of the analyte in the sample, a classification of the analyte, a non-classification of the analyte, and a concentration of the analyte.

3. The method of claim 1, wherein the at least one first test data set comprises one or more of a spectral intensity of the sample and a spectral image representative of the plurality of filtered photons.

4. The method of claim 1, further comprising tuning the conformal filter to a second configuration and generating at least one second test data set representative of a second plurality of filtered photons.

5. The method of claim 1, wherein the tunable filter comprises one or more of a liquid crystal tunable filter, a multi-conjugate tunable filter, an acousto optical tunable filter, a Lyot liquid crystal tunable filter, an Evans Split-Element liquid crystal tunable filter, a Sole liquid crystal tunable filter, and a Ferroelectric liquid crystal tunable filter.

6. The method of claim 1, wherein the tunable filter comprises a Fabry Perot liquid crystal tunable filter.

7. The method of claim 1, wherein illuminating the sample comprises applying wide-field illumination.

8. The method of claim 1, wherein the plurality of interacted photons comprises one or more of photons absorbed by the sample, photons reflected by the sample, photons scattered by the sample, and photons emitted by the sample.

9. The method of claim 1, wherein analyzing the at least one first test data set comprises applying at least one optical computation to the at least one first test data set.

10. The method of claim 9, wherein the at least one first data set comprises a first reflectance image (T1) and a second reflectance image (T2) and the at least one optical computation comprises one or more of T1, T1−T2, and (T1−T2)/(T1+T2).

11. The method of claim 1, further comprising configuring the conformal filter for the analyte by:
tuning the conformal filter to the first configuration to filter the interacted photons conforming to the at least one spectral shape associated with the analyte;
generating at least one reference data set comprising a sample reference data set corresponding to the sample and a matrix reference data set corresponding to a matrix;
determining a tolerance level for the at least one reference data set
applying the tolerance level to the at least one reference data set to determine if the tolerance level is satisfied; and
repeating the generating, the determining, and the applying operations for at least one other tunable filter configuration in response to the at least one reference data set not satisfying the tolerance level.

12. The method of claim 11, further comprising applying at least one optical computation to the at least one reference data set.

13. The method of claim 12, wherein the at least one reference data set comprises a first reflectance image (T1) and a second reflectance image (T2) and the at least one optical computation further comprises one or more of T1, T1−T2, and (T1−T2)/(T1+T2).

14. The method of claim 11, further comprising applying at least one chemometric technique to the at least one reference data set.

15. The method of claim 14, wherein the chemometric technique is selected from the group consisting of a correlation analysis, a principle component analysis, a principle component regression analysis, a partial least squares analysis, a multivariate curve resolution analysis, a Mahalanobis distance analysis, a Euclidian distance analysis, a band target entropy analysis, a band target energy minimization analysis, a partial least squares discriminant analysis, an adaptive subspace detection analysis, and combinations thereof.

16. The method of claim 11, wherein applying a tolerance level to the least one reference data set comprises applying at least one figure of merit.

17. The method of claim 16, wherein the at least one figure of merit comprises one or more of standard error of calibration (SEC), standard error of prediction (SEP), 1-AUROC, and optical throughput (% T).

18. The method of claim 11, wherein the at least one reference data set further comprises at least one reference spectrum representative of the sample and at least one reflectance spectrum representative of the matrix.

19. The method of claim 11, wherein the reference data set further comprises at least one reference image comprising the sample and the matrix.

20. The method of claim 19, further comprising:
selecting a first region of interest and a second region of interest in the at least one reference image, wherein the first region of interest corresponds to the sample and the second region of interest corresponds to the matrix;
extracting spectral information from the first and second regions of interest; and
applying a chemometric technique to the spectral information.

21. A system comprising:
a conformal filter comprising a tunable filter having a plurality of filter stages configured to tune the conformal filter to a plurality of configurations to filter interacted photons to generate a plurality of filtered photons conforming to at least one spectral shape associated with an analyte; and
a look-up table comprising at least one voltage associated with each of the plurality of filter stages, wherein each voltage, when applied to each of the plurality of filter stages, tunes the conformal filter to a spectral shape associated with the analyte.

22. The system of claim 21, wherein the tunable filter further comprises one or more of a liquid crystal tunable filter, a multi-conjugate tunable filter, an acousto optical tunable filter, a Lyot liquid crystal tunable filter, an Evans Split-Element liquid crystal tunable filter, a Sole liquid crystal tunable filter, and a Ferroelectric liquid crystal tunable filter.

23. The system of claim 21, wherein the tunable filter comprises a Fabry Perot liquid crystal tunable filter.

24. The system of claim 21, further comprising at least one illumination source configured to illuminate a sample and generate at least one plurality of interacted photons.

25. The system of claim 24, wherein the illumination source comprises a broadband light source.

26. The system of claim 25, wherein the broadband light source comprises one or more of a quartz tungsten halogen lamp, a high-pressure mercury arc lamp, solar radiation, a light emitting diode, and a blackbody emitter.

27. The system of claim 26, further comprising a collection lens configured to collect at least one plurality of interacted photons and pass the at least one plurality of interacted photons to the conformal filter.

28. The system of claim 21, further comprising a detector configured to detect the filtered photons and generate at least one test data set representative of the sample.

29. The system of claim 21, wherein the detector is selected from the group consisting of an InGaAs detector, a CCD detector, a CMOS detector, an InSb detector, an MCT detector, and combinations thereof.

30. A system comprising:
a processor; and
a non-transitory processor-readable storage medium in operable communication with the processor, wherein the storage medium contains one or more programming instructions that, when executed, cause the processor to perform the following:
tune a conformal filter comprising a tunable filter having a plurality of filter stages to a first configuration conforming to at least one spectral shape associated with an analyte to generate a plurality of filtered photons by:
searching a look-up table comprising at least one voltage associated with each stage of the plurality of filter states corresponding to the analyte, wherein each voltage is configured to cause the tunable filter to conform to the spectral shape associated with the analyte; and
applying the at least one voltage to each filter stage;
generate at least one test data set representative of the plurality of filtered photons; and
analyze the at least one test data set to determine at least one characteristic of the analyte.

31. The system of claim 30, wherein the storage medium further contains one or more programming instructions that, when executed, cause the processor to:
- tune the conformal filter to a first configuration to filter the interacted photons conforming to at least one spectral shape associated with the analyte;
- generate at least one reference data set comprising a first reference data set corresponding to the sample and a second reference data set corresponding to a matrix;
- determine a tolerance level for the at least one reference data set;
- apply the tolerance level to the at least one reference data set to determine if the tolerance level is satisfied; and
- repeat steps the generating, the determining and the applying operations for at least one other tunable filter configuration in response to the at least one reference data set not satisfying the tolerance level.

32. The system of claim 31, wherein the storage medium further contains one or more programming instructions that, when executed, cause the processor to apply at least one figure of merit to determine if a tolerance level is satisfied.

33. The system of claim 31, wherein the storage medium further contains one or more programming instructions that, when executed, cause the processor to apply at least one optical computation to the reference data set.

34. The system of claim 31, wherein the storage medium further contains one or more programming instructions that, when executed, cause the processor to apply at least one chemometric technique to the reference data set.

* * * * *